(12) United States Patent
Jung et al.

(10) Patent No.: US 10,947,602 B2
(45) Date of Patent: Mar. 16, 2021

(54) METHODS OF MAKING GRAY LEAF SPOT RESISTANT MAIZE

(71) Applicant: PIONEER HI-BRED INTERNATIONAL, INC., Johnston, IA (US)

(72) Inventors: Mark Timothy Jung, Urbandale, IA (US); Leandro Daniel Perugini, Urbandale, IA (US); Petra J. Wolters, Kennett Square, PA (US)

(73) Assignee: PIONEER HI-BRED INTERNATIONAL, INC.

( * ) Notice: Subject to any disclaimer, the term of this patent is extended or adjusted under 35 U.S.C. 154(b) by 4 days.

(21) Appl. No.: 16/315,727

(22) PCT Filed: Jun. 26, 2017

(86) PCT No.: PCT/US2017/039249
§ 371 (c)(1),
(2) Date: Jan. 7, 2019

(87) PCT Pub. No.: WO2018/013323
PCT Pub. Date: Jan. 18, 2018

(65) Prior Publication Data
US 2019/0300969 A1    Oct. 3, 2019

Related U.S. Application Data

(60) Provisional application No. 62/360,585, filed on Jul. 11, 2016.

(51) Int. Cl.
*C12Q 1/68*    (2018.01)
*A01H 5/10*    (2018.01)
*C12Q 1/6895*  (2018.01)
*A01H 1/04*    (2006.01)

(52) U.S. Cl.
CPC .......... *C12Q 1/6895* (2013.01); *A01H 1/04* (2013.01); *A01H 5/10* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2004/0034888 A1 | 2/2004 | Liu et al. |
| 2009/0172845 A1 | 7/2009 | Li et al. |
| 2014/0109257 A1 | 4/2014 | Butruille et al. |
| 2015/0322536 A1 | 11/2015 | Kerns et al. |
| 2016/0024519 A1 | 1/2016 | Kerns et al. |

FOREIGN PATENT DOCUMENTS

WO    2015095777 A1    6/2015

OTHER PUBLICATIONS

Benson, Jacqueline, et al.: "Resistance to Gray Leaf Spot of Maize: Genetic Architecture and Mechanisms Elucidated through Nested Association Mapping and Near-Isogenic Line Analysis", PLoS Genetics, Mar. 12, 2015 (Mar. 12, 2015), vol. 11, No. 3, pp. 1-23.
International Search Report and Written Opinion for International Application No. PCT/US2017/039249, dated Oct. 6, 2017.

*Primary Examiner* — Medina A Ibrahim

(57) ABSTRACT

Compositions and methods useful in identifying and selecting maize plants with increased resistance to gray leaf spot are provided herein. The methods use molecular genetic markers within a QTL region located on chromosome 4 to identify and select plants with increased resistance to gray leaf spot, and plants comprising the QTL allele associated with increased resistance to gray leaf spot can be crossed to other maize plants to incorporate the increased resistance into other maize lines or varieties.

3 Claims, No Drawings
Specification includes a Sequence Listing.

METHODS OF MAKING GRAY LEAF SPOT RESISTANT MAIZE

CROSS-REFERENCE TO RELATED APPLICATIONS

This application claims priority to International Patent Application PCT/US2017/039249 filed on Jun. 26, 2017, which claims priority to U.S. Provisional Application No. 62/360,585, filed Jul. 11, 2016, the contents of which are herein incorporated by reference in their entirety.

FIELD

The present disclosure relates to compositions and methods useful in enhancing resistance to gray leaf spot in maize plants.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of BB2457WOPCT_SequenceListing_ST25.txt, a creation date of May 22, 2017 and a size of 14.1 Kb. The sequence listing filed via EFS-Web is part of the specification and is hereby incorporated in its entirety by reference herein.

BACKGROUND

Maize is one of the most important food sources for humans and animals. Many environmental stress factors affect maize plants, impacting maize production and availability. For example, maize crops are often severely affected by gray leaf spot (GLS) caused by the fungal pathogen *Cercospora zeae-maydis* or *Cercospora zeina* (herein referred to as *Cercospora* spp.).

GLS is a global problem with prevalence in Africa; North, Central and South America; and Asia. *Cercospora* spp. overwinters in field debris and requires moisture, usually in the form of heavy fog, dew, or rain, to spread its spores and infect maize. *Cercospora* spp. infection in maize elicits an increased allocation of the plant's resources to protect against damaged leaf tissue, leading to elevated risk of root and stalk rot, and reduced allocation of resources to grain filling, which ultimately results in even greater crop losses. Symptoms typically include elongated, gray coloured lesions of about 1-3 mm in width and ranging from 5 to 70 mm in length occurring on leaf material. Lesions have also been noted to occur on stems during severe cases of infection. Furthermore, *Cercospora* spp. infection reduces grain yield and silage quality. GLS may result in yield loss of up to 68%. Therefore, reduction of the susceptibility of maize to GLS is understandably of importance.

Some commonly used GLS control methods are fungicides, crop rotation, tillage and field sanitation. Some of the disadvantages of these methods are that they are relatively expensive, ineffective or harmful to the environment. However, the most effective and most preferred method of control for GLS is the planting of resistant hybrids.

The use of phenotypic selection to introgress the GLS trait from a resistant variety into a susceptible variety can be time consuming and difficult. GLS is sensitive to environmental conditions and requires high humidity and extended leaf wetness. This sensitivity makes it difficult to reliably select for resistance to GLS from year to year based solely on phenotype (Lehmensiek et al., *Theor. Appl. Genet.* 103:797-803 (2001)). Specialized disease screening sites can be costly to operate, and plants must be grown to maturity in order to classify the level of resistance.

Selection through the use of molecular markers associated with GLS resistance has the advantage of permitting at least some selection based solely on the genetic composition of the progeny. Thus, GLS resistance can be measured very early on in the plant life cycle, even as early as the seed stage. The increased rate of selection that can be obtained through the use of molecular markers associated with the GLS resistance trait means that plant breeding for GLS resistance can occur at a faster rate and that commercially acceptable GLS resistant plants can be developed more quickly.

There is a need for commercially acceptable hybrid and inbred lines displaying a relatively high level of resistance to GLS associated with *Cercospora zeina*. Thus, methods for identifying maize plants with resistance to GLS with which the aforesaid disadvantages could be overcome or at least minimised are of interest. Also of interest are molecular genetic markers for screening maize plants displaying varying levels of resistance to GLS.

SUMMARY

Compositions and methods for identifying and/or selecting (i.e. obtaining) maize plants having increased resistance to gray leaf spot are provided herein.

In one embodiment, a method of identifying and/or selecting a maize plant with increased resistance to gray leaf spot is presented herein, the method comprising the steps of: (a) screening a population with a marker located within an interval on chromosome 4 comprising and flanked by PHM6764-7 and PHM289-1 to determine if one or more maize plants from the population comprises a QTL allele associated with increased resistance to gray leaf spot, wherein the QTL allele comprises a "C" at PHM1963-15 and one or more of the following: a "T" at PHM521-8; a "G" at PHM12024-9; a "T" at PHM199-23; a "T" at PHMGLS_01; a "C" at PHMGLS_07; a "G" at PHMGLS_14; a "C" at PHMGLS_19; a "C" at PHMGLS_21; a "C" at PHMGLS_45; a "A" at PHMC001YAR; a "C" at PHM5013-12; a "T" at PHM586-10; a "A" at PHM15534-13; a "G" at PHM18451-2; and a "C" at PHM289-20; and (b) selecting from said population at least one maize plant comprising the QTL allele. The marker may be located within an interval on chromosome 4 comprising and flanked by PHM521-8 and PHM18451-2. The method may further comprise: (c) crossing the maize plant to a second maize plant; and (d) obtaining a progeny plant that has the favorable QTL allele. The method may include selecting a maize plant from a breeding program if the QTL allele is detected or counter-selecting a maize plant if the QTL allele is not detected. In one aspect, the QTL allele associated with increased resistance to gray leaf spot comprises: a "T" at PHM521-8; a "G" at PHM12024-9; a "T" at PHM199-23; a "T" at PHMGLS_01; a "C" at PHMGLS_07; a "G" at PHMGLS_14; a "C" at PHMGLS_19; a "C" at PHMGLS_21; a "C" at PHMGLS_45; a "A" at PHMC001YAR; a "C" at PHM5013-12; a "T" at PHM586-10; a "C" at PHM1963-15; a "A" at PHM15534-13; a "G" at PHM18451-2; and a "C" at PHM289-20.

In another embodiment, a method of identifying and/or selecting a maize plant that displays increased resistance to gray leaf spot is provided herein. The method comprises the steps of (a) detecting in a maize plant an allele of a marker locus, wherein said marker locus is located within a chromosomal interval on chromosome 4 comprising and flanked by PHM6764-7 and PHM289-1, and said allele is associated with a haplotype comprising a "T" at PHM521-8; a "G" at PHM12024-9; a "T" at PHM199-23; a "T" at PHMGLS_01; a "C" at PHMGLS_07; a "G" at PHMGLS_14; a "C" at PHMGLS_19; a "C" at PHMGLS_21; a "C" at PHMGLS_45; a "A" at PHMC001YAR; a "C" at PHM5013-12; a "T" at PHM586-10; a "C" at PHM1963-15; a "A" at PHM15534-13; a "G" at PHM18451-2; and a "C" at PHM289-20; and (b) selecting a maize plant that has the allele of the marker locus that is associated with the haplotype comprising a "T" at PHM521-8; a "G" at PHM12024-9; a "T" at PHM199-23; a "T" at PHMGLS_01; a "C" at PHMGLS_07; a "G" at PHMGLS_14; a "C" at PHMGLS_19; a "C" at PHMGLS_21; a "C" at PHMGLS_45; a "A" at PHMC001YAR; a "C" at PHM5013-12; a "T" at PHM586-10; a "C" at PHM1963-15; a "A" at PHM15534-13; a "G" at PHM18451-2; and a "C" at PHM289-20. The marker locus may further be refined to a chromosomal interval on chromosome 4 comprising and flanked by PHM521-8 and PHM18451-2. The method may further comprise: (c) crossing the maize plant to a second maize plant; and (d) obtaining a progeny plant that has the allele associated with the haplotype comprising a "T" at PHM521-8; a "G" at PHM12024-9; a "T" at PHM199-23; a "T" at PHMGLS_01; a "C" at PHMGLS_07; a "G" at PHMGLS_14; a "C" at PHMGLS_19; a "C" at PHMGLS_21; a "C" at PHMGLS_45; a "A" at PHMC001YAR; a "C" at PHM5013-12; a "T" at PHM586-10; a "C" at PHM1963-15; a "A" at PHM15534-13; a "G" at PHM18451-2; and a "C" at PHM289-20.

In another embodiment, a method of identifying and/or selecting a maize plant that displays increased resistance to gray leaf spot is provided herein. The method comprises the steps of (a) detecting in a maize plant a QTL allele comprising a "C" at PHM1963-15 and one or more of the following: a "T" at PHM521-8; a "G" at PHM12024-9; a "T" at PHM199-23; a "T" at PHMGLS_01; a "C" at PHMGLS_07; a "G" at PHMGLS_14; a "C" at PHMGLS_19; a "C" at PHMGLS_21; a "C" at PHMGLS_45; a "A" at PHMC001YAR; a "C" at PHM5013-12; a "T" at PHM586-10; a "A" at PHM15534-13; a "G" at PHM18451-2; and a "C" at PHM289-20; wherein said QTL allele is located on chromosome 4 in an interval defined by and including PHM6764-7 and PHM289-1; and (b) selecting a maize plant that has the QTL allele. The QTL allele may be located on chromosome 4 in an interval defined by and including PHM521-8 and PHM18451-2. The method may further comprise: (c) crossing the maize plant to a second maize plant; and (d) obtaining a progeny plant that has the QTL allele. The QTL allele may further comprise a "T" at PHM521-8; a "G" at PHM12024-9; a "T" at PHM199-23; a "T" at PHMGLS_01; a "C" at PHMGLS_07; a "G" at PHMGLS_14; a "C" at PHMGLS_19; a "C" at PHMGLS_21; a "C" at PHMGLS_45; a "A" at PHMC001YAR; a "C" at PHM5013-12; a "T" at PHM586-10; a "C" at PHM1963-15; a "A" at PHM15534-13; a "G" at PHM18451-2; and a "C" at PHM289-20.

In another embodiment, a method of identifying and/or selecting a maize plant that displays increased resistance to gray leaf spot is provided herein. The method comprises the steps of (a) detecting in a maize plant a "T" at PHM521-8; a "G" at PHM12024-9; a "T" at PHM199-23; a "T" at PHMGLS_01; a "C" at PHMGLS_07; a "G" at PHMGLS_14; a "C" at PHMGLS_19; a "C" at PHMGLS_21; a "C" at PHMGLS_45; a "A" at PHMC001YAR; a "C" at PHM5013-12; a "T" at PHM586-10; a "C" at PHM1963-15; a "A" at PHM15534-13; a "G" at PHM18451-2; and a "C" at PHM289-20; and (b) selecting a maize plant that has a "T" at PHM521-8; a "G" at PHM12024-9; a "T" at PHM199-23; a "T" at PHMGLS_01; a "C" at PHMGLS_07; a "G" at PHMGLS_14; a "C" at PHMGLS_19; a "C" at PHMGLS_21; a "C" at PHMGLS_45; a "A" at PHMC001YAR; a "C" at PHM5013-12; a "T" at PHM586-10; a "C" at PHM1963-15; a "A" at PHM15534-13; a "G" at PHM18451-2; and a "C" at PHM289-20, wherein said maize plant has increased resistance to gray leaf spot. The method may further comprise: (c) crossing the maize plant to a second maize plant; and (d) obtaining a progeny plant that has a "T" at PHM521-8; a "G" at PHM12024-9; a "T" at PHM199-23; a "T" at PHMGLS_01; a "C" at PHMGLS_07; a "G" at PHMGLS_14; a "C" at PHMGLS_19; a "C" at PHMGLS_21; a "C" at PHMGLS_45; a "A" at PHMC001YAR; a "C" at PHM5013-12; a "T" at PHM586-10; a "C" at PHM1963-15; a "A" at PHM15534-13; a "G" at PHM18451-2; and a "C" at PHM289-20.

Plants identified and/or selected using the methods described herein are also provided.

BRIEF DESCRIPTION OF THE SEQUENCE LISTING

The disclosure can be more fully understood from the following detailed description and the Sequence Listing which forms a part of this application.

The sequence descriptions and Sequence Listing attached hereto comply with the rules governing nucleotide and/or amino acid sequence disclosures in patent applications as set forth in 37 C.F.R. § 1.821 1.825. The Sequence Listing contains the one letter code for nucleotide sequence characters and the three letter codes for amino acids as defined in conformity with the IUPAC IUBMB standards described in *Nucleic Acids Res.* 13:3021 3030 (1985) and in the *Biochemical J.* 219 (2):345 373 (1984) which are herein incorporated by reference. The symbols and format used for nucleotide and amino acid sequence data comply with the rules set forth in 37 C.F.R. § 1.822.

SEQ ID NO:1 is the reference sequence for marker PHM6764-7.

SEQ ID NO:2 is the reference sequence for marker PHM16360-9.

SEQ ID NO:3 is the reference sequence for marker PHM521-8.

SEQ ID NO:4 is the reference sequence for marker PHM586-10.

SEQ ID NO:5 is the reference sequence for marker PHM289-20.

SEQ ID NO:6 is the reference sequence for marker PHM12024-9.

SEQ ID NO:7 is the reference sequence for marker PHM199-23.

SEQ ID NO:8 is the reference sequence for marker PHM1963-15.

SEQ ID NO:9 is the reference sequence for marker PHM18451-2.

SEQ ID NO:10 is the reference sequence for marker PZE-104068674.

SEQ ID NO:11 is the reference sequence for marker SYN25809.

SEQ ID NO:12 is the reference sequence for marker PZE-104069351.

SEQ ID NO:13 is the reference sequence for marker PZE-104069548.

SEQ ID NO:14 is the reference sequence for marker PZE-104069570.

SEQ ID NO:15 is the reference sequence for marker PZE-104069652.

SEQ ID NO:16 is the reference sequence for marker SYN21168.

SEQ ID NO:17 is the reference sequence for marker SYN4720.

SEQ ID NO:18 is the reference sequence for marker SYN4714.

SEQ ID NO:19 is the reference sequence for marker PZE-104070450.

SEQ ID NO:20 is the reference sequence for marker PHMGLS_01.

SEQ ID NO:21 is the reference sequence for marker PHMGLS_07.

SEQ ID NO:22 is the reference sequence for marker PHMGLS_14.

SEQ ID NO:23 is the reference sequence for marker PHMGLS_19.

SEQ ID NO:24 is the reference sequence for marker PHMGLS_21.

SEQ ID NO:25 is the reference sequence for marker PHMGLS_45.

SEQ ID NO:26 is the reference sequence for marker PHMC001YAR.

SEQ ID NO:27 is the reference sequence for marker PHM5013-12.

SEQ ID NO:28 is the reference sequence for marker PHM15534-13.

DETAILED DESCRIPTION

Maize marker loci that demonstrate statistically significant co-segregation with the gray leaf spot resistance trait are provided herein. Detection of these loci or additional linked loci can be used in marker assisted selection as part of a maize breeding program to produce maize plants that have resistance to gray leaf spot.

The following definitions are provided as an aid to understand the present disclosure.

It is to be understood that the disclosure is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the disclosure pertains. Although any methods and materials similar or equivalent to those described herein can be used for testing of the subject matter recited in the current disclosure, the preferred materials and methods are described herein. In describing and claiming the subject matter of the current disclosure, the following terminology will be used in accordance with the definitions set out below.

The term "allele" refers to one of two or more different nucleotide sequences that occur at a specific locus.

"Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. Public assemblies can be found using the Maize Genome Browser, which is publicly available on the internet.

An allele is "associated with" a trait when it is part of or linked to a DNA sequence or allele that affects the expression of the trait. The presence of the allele is an indicator of how the trait will be expressed.

A "BAC", or bacterial artificial chromosome, is a cloning vector derived from the naturally occurring F factor of *Escherichia coli*, which itself is a DNA element that can exist as a circular plasmid or can be integrated into the bacterial chromosome. BACs can accept large inserts of DNA sequence. In maize, a number of BACs each containing a large insert of maize genomic DNA from maize inbred line B73, have been assembled into contigs (overlapping contiguous genetic fragments, or "contiguous DNA"), and this assembly is available publicly on the internet.

A BAC fingerprint is a means of analyzing similarity between several DNA samples based upon the presence or absence of specific restriction sites (restriction sites being nucleotide sequences recognized by enzymes that cut or "restrict" the DNA). Two or more BAC samples are digested with the same set of restriction enzymes and the sizes of the fragments formed are compared, usually using gel separation.

"Backcrossing" refers to the process whereby hybrid progeny are repeatedly crossed back to one of the parents. In a backcrossing scheme, the "donor" parent refers to the parental plant with the desired gene/genes, locus/loci, or specific phenotype to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in *Techniques et Utilisations des Marqueurs Moleculaires Les Colloques*, Vol. 72, pp. 45-56, and Openshaw et al., (1994) Marker-assisted Selection in *Backcross Breeding, Analysis of Molecular Marker Data*, pp. 41-43. The initial cross gives rise to the $F_1$ generation; the term "$BC_1$" then refers to the second use of the recurrent parent, "$BC_2$" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" is a single piece of coiled DNA containing many genes that act and move as a unity during cell division and therefore can be said to be linked. It can also be referred to as a "linkage group".

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful with respect to the subject matter of the current disclosure when they demonstrate a significant probability of co-segregation (linkage) with a desired trait (e.g., resistance to gray leaf spot). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "complement" refers to a nucleotide sequence that is complementary to a given nucleotide sequence, i.e. the sequences are related by the Watson-Crick base-pairing rules.

The term "contiguous DNA" refers to an uninterrupted stretch of genomic DNA represented by partially overlapping pieces or contigs.

When referring to the relationship between two genetic elements, such as a genetic element contributing to gray leaf spot resistance and a proximal marker, "coupling" phase linkage indicates the state where the "favorable" allele at the gray leaf spot resistance locus is physically associated on the same chromosome strand as the "favorable" allele of the respective linked marker locus. In coupling phase, both favorable alleles are inherited together by progeny that inherit that chromosome strand.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

A plant referred to herein as "diploid" has two sets (genomes) of chromosomes.

A plant referred to herein as a "doubled haploid" is developed by doubling the haploid set of chromosomes (i.e., half the normal number of chromosomes). A doubled haploid plant has two identical sets of chromosomes, and all loci are considered homozygous.

An "elite line" is any line that has resulted from breeding and selection for superior agronomic performance.

An "exotic maize strain" or an "exotic maize germplasm" is a strain derived from a maize plant not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

A "favorable allele" is the allele at a particular locus (a marker, a QTL, etc.) that confers, or contributes to, an agronomically desirable phenotype, e.g., gray leaf spot resistance, and that allows the identification of plants with that agronomically desirable phenotype. A favorable allele of a marker is a marker allele that segregates with the favorable phenotype.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (their recombination frequencies). Alleles can be detected using DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify positions of markers and other loci of interest on each individual genetic map.

The order of loci should not change between maps, although frequently there are small changes in marker orders due to e.g. markers detecting alternate duplicate loci in different populations, differences in statistical approaches used to order the markers, novel mutation or laboratory error.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci. Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment.

The term "heterogeneity" is used to indicate that individuals within the group differ in genotype at one or more specific loci.

The heterotic response of material, or "heterosis", can be defined by performance which exceeds the average of the parents (or high parent) when crossed to other dissimilar or unrelated groups.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Corn Belt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) *Crop Sci:* 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Leaming Corn.

An individual is "heterozygous" if more than one allele type is present at a given locus (e.g., a diploid individual with one copy each of two different alleles).

The term "homogeneity" indicates that members of a group have the same genotype at one or more specific loci.

An individual is "homozygous" if the individual has only one type of allele at a given locus (e.g., a diploid individual has a copy of the same allele at a locus for each of two homologous chromosomes).

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" can refer to any of following maps: IBM, IBM2, IBM2 neighbors, IBM2 FPC0507, IBM2 2004 neighbors, IBM2 2005 neighbors, IBM2 2005 neighbors frame, IBM2 2008 neighbors, IBM2 2008 neighbors frame, or the latest version on the maizeGDB website. IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic maps or physical maps, cleaned date, or the use of new algorithms.

The term "inbred" refers to a line that has been bred for genetic homogeneity.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an $F_2$; the IBM2 maps consist of multiple meioses). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231 (1968). When $r^2=1$, complete LD exists between the two marker loci, meaning that the markers have not been separated by recombination and have the same allele frequency. The $r^2$ value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

"Maize" refers to a plant of the *Zea mays* L. ssp. *mays* and is also known as "corn".

The term "maize plant" includes whole maize plants, maize plant cells, maize plant protoplast, maize plant cell or maize tissue culture from which maize plants can be regenerated, maize plant calli, maize plant clumps and maize plant cells that are intact in maize plants or parts of maize plants, such as maize seeds, maize cobs, maize flowers, maize cotyledons, maize leaves, maize stems, maize buds, maize roots, maize root tips and the like.

A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A maize plant "derived from an inbred in the Stiff Stalk Synthetic population" may be a hybrid.

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

An allele "positively" correlates with a trait when it is linked to it and when presence of the allele is an indicator that the desired trait or trait form will occur in a plant comprising the allele.

The "probability value" or "p-value" is the statistical likelihood that the particular combination of a phenotype and the presence or absence of a particular marker allele is random. Thus, the lower the probability score, the greater the likelihood that a locus and a phenotype are associated. The probability score can be affected by the proximity of the first locus (usually a marker locus) and the locus affecting the phenotype, plus the magnitude of the phenotypic effect (the change in phenotype caused by an allele substitution). In some aspects, the probability score is considered "significant" or "nonsignificant". In some embodiments, a probability score of 0.05 (p=0.05, or a 5% probability) of random assortment is considered a significant indication of association. However, an acceptable probability can be any probability of less than 50% (p=0.5). For example, a significant probability can be less than 0.25, less than 0.20, less than 0.15, less than 0.1, less than 0.05, less than 0.01, or less than 0.001.

A "production marker" or "production SNP marker" is a marker that has been developed for high-throughput purposes. Production SNP markers are developed to detect specific polymorphisms and are designed for use with a variety of chemistries and platforms. The marker names used here begin with a PHM prefix to denote 'Pioneer Hi-Bred Marker', followed by a number that is specific to the sequence from which it was designed, followed by a "." or a "-" and then a suffix that is specific to the DNA polymorphism. A marker version can also follow (A, B, C etc.) that denotes the version of the marker designed to that specific polymorphism.

The term "progeny" refers to the offspring generated from a cross.

A "progeny plant" is a plant generated from a cross between two plants.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question.

A "reference sequence" or a "consensus sequence" is a defined sequence used as a basis for sequence comparison. The reference sequence for a PHM marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

The phrase "Gray Leaf Spot" or "GLS" refers to a cereal disease caused by the fungal pathogen *Cercospora zeae-maydis*, which characteristically produces long, rectangular, grayish-tan leaf lesions which run parallel to the leaf vein.

"Newly conferred resistance" or "enhanced resistance" or "increased resistance" in a maize plant to GLS is an indication that the maize plant is less affected with respect to yield and/or survivability or other relevant agronomic measures, upon introduction of the causative agents of that disease, e.g., *Cercospora zeae-maydis*. "Increased resistance" indicates that the infected plant produces better yield of maize than another, similarly treated, more susceptible plant. That is, the conditions cause a reduced decrease in maize survival and/or yield in a maize plant with increased resistance (or tolerance), as compared to a susceptible maize plant.

One of skill will appreciate that maize plant resistance to GLS varies widely, can represent a spectrum of more resistant or less resistant phenotypes, and can vary depending on the severity of the infection. However, by simple observation, one of skill can determine the relative resistance or susceptibility of different plants, plant lines or plant families to GLS, and furthermore, will also recognize the phenotypic gradations of "resistant". For example, a 1 to 9 visual rating indicating the resistance to GLS can be used. A higher score indicates a higher resistance. Data should be collected only when sufficient selection pressure exists in the experiment measured.

A "topcross test" is a test performed by crossing each individual (e.g. a selection, inbred line, clone or progeny individual) with the same pollen parent or "tester", usually a homozygous line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances. Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Sequence alignments and percent identity calculations may be determined using a variety of comparison methods designed to detect homologous sequences including, but not limited to, the MEGALIGN® program of the LASER-GENE® bioinformatics computing suite (DNASTAR® Inc., Madison, Wis.). Unless stated otherwise, multiple alignment of the sequences provided herein were performed using the CLUSTAL V method of alignment (Higgins and Sharp, CABIOS. 5:151 153 (1989)) with the default parameters (GAP PENALTY=10, GAP LENGTH PENALTY=10). Default parameters for pairwise alignments and calculation of percent identity of protein sequences using the CLUSTAL V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the CLUSTAL V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Genetic Mapping

It has been recognized for quite some time that specific genetic loci correlating with particular phenotypes, such as resistance to gray leaf spot, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as the gray leaf spot resistance trait. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference. Two such methods used to detect trait loci of interest are: 1) Population-based association analysis (i.e. association mapping) and 2) Traditional linkage analysis.

Association Mapping

Understanding the extent and patterns of linkage disequilibrium (LD) in the genome is a prerequisite for developing efficient association approaches to identify and map quantitative trait loci (QTL). Linkage disequilibrium (LD) refers to the non-random association of alleles in a collection of individuals. When LD is observed among alleles at linked loci, it is measured as LD decay across a specific region of a chromosome. The extent of the LD is a reflection of the recombinational history of that region. The average rate of LD decay in a genome can help predict the number and density of markers that are required to undertake a genome-wide association study and provides an estimate of the resolution that can be expected.

Association or LD mapping aims to identify significant genotype-phenotype associations. It has been exploited as a powerful tool for fine mapping in outcrossing species such as humans (Corder et al. (1994) "Protective effect of apolipoprotein-E type-2 allele for late-onset Alzheimer-disease," Nat Genet 7:180-184; Hastbacka et al. (1992) "Linkage disequilibrium mapping in isolated founder populations: diastrophic dysplasia in Finland," *Nat Genet* 2:204-211; Kerem et al. (1989) "Identification of the cystic fibrosis gene: genetic analysis," *Science* 245:1073-1080) and maize (Remington et al., (2001) "Structure of linkage disequilibrium and phenotype associations in the maize genome," *Proc Natl Acad Sci USA* 98:11479-11484; Thornsberry et al. (2001) "Dwarf8 polymorphisms associate with variation in flowering time," *Nat Genet* 28:286-289; reviewed by Flint-Garcia et al. (2003) "Structure of linkage disequilibrium in plants," *Annu Rev Plant Biol.* 54:357-374), where recombination among heterozygotes is frequent and results in a rapid decay of LD. In inbreeding species where recombination among homozygous genotypes is not genetically detectable, the extent of LD is greater (i.e., larger blocks of linked markers are inherited together) and this dramatically enhances the detection power of association mapping (Wall and Pritchard (2003) "Haplotype blocks and linkage disequilibrium in the human genome," *Nat Rev Genet* 4:587-597).

The recombinational and mutational history of a population is a function of the mating habit as well as the effective size and age of a population. Large population sizes offer enhanced possibilities for detecting recombination, while older populations are generally associated with higher levels of polymorphism, both of which contribute to observably accelerated rates of LD decay. On the other hand, smaller effective population sizes, e.g., those that have experienced a recent genetic bottleneck, tend to show a slower rate of LD decay, resulting in more extensive haplotype conservation (Flint-Garcia et al. (2003) "Structure of linkage disequilibrium in plants," *Annu Rev Plant Biol.* 54:357-374).

Elite breeding lines provide a valuable starting point for association analyses. Association analyses use quantitative phenotypic scores (e.g., disease tolerance rated from one to nine for each maize line) in the analysis (as opposed to looking only at tolerant versus resistant allele frequency distributions in intergroup allele distribution types of analysis). The availability of detailed phenotypic performance data collected by breeding programs over multiple years and environments for a large number of elite lines provides a valuable dataset for genetic marker association mapping analyses. This paves the way for a seamless integration between research and application and takes advantage of historically accumulated data sets. However, an understanding of the relationship between polymorphism and recombination is useful in developing appropriate strategies for efficiently extracting maximum information from these resources.

This type of association analysis neither generates nor requires any map data, but rather is independent of map position. This analysis compares the plants' phenotypic score with the genotypes at the various loci. Subsequently, any suitable maize map (for example, a composite map) can optionally be used to help observe distribution of the identified QTL markers and/or QTL marker clustering using previously determined map locations of the markers.

Traditional Linkage Analysis

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Maize marker loci that demonstrate statistically significant co-segregation with the gray leaf spot resistance trait, as determined by traditional linkage analysis and by whole genome association analysis, are provided herein. Detection of these loci or additional linked loci can be used in marker assisted maize breeding programs to produce plants having resistance to gray leaf spot.

Activities in marker assisted maize breeding programs may include but are not limited to: selecting among new breeding populations to identify which population has the highest frequency of favorable nucleic acid sequences based on historical genotype and agronomic trait associations, selecting favorable nucleic acid sequences among progeny in breeding populations, selecting among parental lines based on prediction of progeny performance, and advancing lines in germplasm improvement activities based on presence of favorable nucleic acid sequences.

QTL Locations

A QTL on chromosome 4 was identified as being associated with the gray leaf spot resistance trait using traditional linkage mapping and then validated (Examples 1 and 2). While the QTL is in the same location as that described in US2009172845, marker analysis and identity by descent studies show that the QTL allele described herein is from a different source.

Chromosomal Intervals

Chromosomal intervals that correlate with the gray leaf spot resistance trait are provided. A variety of methods well known in the art are available for identifying chromosomal intervals. The boundaries of such chromosomal intervals are drawn to encompass markers that will be linked to the gene(s) controlling the trait of interest. In other words, the chromosomal interval is drawn such that any marker that lies within that interval (including the terminal markers that define the boundaries of the interval) can be used as a marker for the gray leaf spot resistance trait. Tables 1 and 3 identify markers within the chromosome 4 QTL region that are shown herein to associate with the gray leaf spot resistance trait and that are linked to a gene(s) controlling gray leaf spot resistance. Reference sequences for each of the markers are represented by SEQ ID NOs:1-9.

Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice that which is presented in the current disclosure.

The chromosome 4 interval may encompass any of the markers identified herein as being associated with the gray leaf spot resistance trait including: PHM6764-7, PHM16360-9, PHM521-8, PHM586-10, PHM289-20, PHM12024-9, PHM199-23, PHMGLS_01, PHMGLS_07, PHMGLS_14, PHMGLS_19, PHMGLS_21, PHMGLS_45, PHMC001YAR, PHM5013-12, PHM1963-15, and PHM18451-2. The chromosome 4 interval may be defined by markers PHM6764-7 and PHM289-1 (Example 1), which are separated by the greatest distance on the physical map. A subinterval of this region may further be defined by markers PHM521-8 and PHM185451-2. Any marker located within these intervals can find use as a marker for gray leaf spot resistance and can be used in the context of the methods presented herein to identify and/or select maize plants that have resistance to gray leaf spot, whether it is newly conferred or enhanced compared to a control plant.

Chromosomal intervals can also be defined by markers that are linked to (show linkage disequilibrium with) a QTL marker, and $r^2$ is a common measure of linkage disequilibrium (LD) in the context of association studies. If the $r^2$ value of LD between a chromosome 4 marker locus provided herein and another chromosome 4 marker locus in close proximity is greater than ⅓ (Ardlie et al., *Nature Reviews Genetics* 3:299-309 (2002)), the loci are in linkage disequilibrium with one another.

Markers and Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with the gray leaf spot resistance trait, it is important to note that the marker locus is not necessarily responsible for the expression of the gray leaf spot resistant phenotype. For example, it is not a requirement that the marker polynucleotide sequence be part of a gene that is responsible for the gray leaf spot resistant phenotype (for example, is part of the gene open reading frame). The association between a specific marker allele and the gray leaf spot resistance trait is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the parent having resistance to gray leaf spot that is used to create segregating populations. This does not change the fact that the marker can be used to monitor segregation of the phenotype. It only changes which marker allele is considered favorable in a given segregating population.

Methods presented herein include detecting the presence of one or more marker alleles associated with gray leaf spot resistance in a maize plant and then identifying and/or selecting maize plants that have favorable alleles at those marker loci. Markers listed in Tables 1, 2, and 3 have been identified herein as being associated with the gray leaf spot resistance trait and hence can be used to predict gray leaf spot resistance in a maize plant. Any marker within 50 cM, 40 cM, 30 cM, 20 cM, 15 cM, 10 cM, 9 cM, 8 cM, 7 cM, 6 cM, 5 cM, 4 cM, 3 cM, 2 cM, 1 cM, 0.75 cM, 0.5 cM or 0.25 cM (based on a single meiosis based genetic map) of any of the markers in Tables 1 and 3 could also be used to predict gray leaf spot resistance in a maize plant.

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide.* Academic press. pp 75-135).

Various types of SSR markers can be generated, and SSR profiles can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; and Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™. (Qiagen), INVADER®. (Third Wave Technologies) and Invader PLUS®, SNAPSHOT®. (Applied Biosystems), TAQMAN®. (Applied Biosystems) and BEADARRAYS®. (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele 'T' for a specific line or variety with gray leaf spot resistance, but the allele 'T' might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Many of the PHM markers presented herein can readily be used as FLP markers to select for the gene loci on chromosome 4, owing to the presence of insertions/deletion polymorphisms. Primers for the PHM markers can also be used to convert these markers to SNP or other structurally similar or functionally equivalent markers (SSRs, CAPs, indels, etc.), in the same regions. One very productive approach for SNP conversion is described by Rafalski (2002a) *Current opinion in plant biology* 5 (2): 94-100 and also Rafalski (2002b) *Plant Science* 162: 329-333. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically with respect to the fine map information described herein, one can readily use the information provided herein to obtain additional polymorphic SNPs (and other markers) within the region amplified by the primers listed in this disclosure. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

In general, MAS uses polymorphic markers that have been identified as having a significant likelihood of co-segregation with a trait such as the gray leaf spot resistance trait. Such markers are presumed to map near a gene or genes that give the plant its gray leaf spot resistant phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with gray leaf spot resistance can be selected for by detecting one or more marker alleles, and in addition, progeny plants derived from those plants can also be selected. Hence, a plant containing a desired genotype in a given chromosomal region (i.e. a genotype associated with gray leaf spot resistance) is obtained and then crossed to another plant. The progeny of such a cross would then be evaluated genotypically using one or more markers and the progeny plants with the same genotype in a given chromosomal region would then be selected as having gray leaf spot resistance.

Markers were identified from both linkage mapping and association analysis as being associated with the gray leaf spot resistance trait. Reference sequences for the markers are represented by SEQ ID NOs:1-9. SNP positions are identified within the marker sequences.

Methods of identifying and/or selecting maize plants with increased resistance to gray leaf spot may include: (a) screening a population with a marker in the QTL interval to determine if a maize plant from the population has a QTL allele defined herein; (b) detecting a maize plant that has a marker allele associated with the haplotype defined herein; (c) detecting a maize plant that has a QTL allele wherein said QTL allele comprises a "C: at PHM1963-15 and any other allele provided herein; or (d) detecting a maize plant that has a T" at PHM521-8; a "G" at PHM12024-9; a "T" at PHM199-23; a "T" at PHM586-10; a "C" at PHM1963-15; a "G" at PHM18451-2; and a "C" at PHM289-20. A maize plant that is identified may then be selected for further development which may include crossing to a second maize plant and generating a progeny plant.

The skilled artisan would expect that there might be additional polymorphic sites at marker loci in and around the chromosome 4 markers identified herein, wherein one or more polymorphic sites is in linkage disequilibrium (LD) with an allele at one or more of the polymorphic sites in the haplotype and thus could be used in a marker assisted selection program to introgress a QTL allele of interest. Two particular alleles at different polymorphic sites are said to be in LD if the presence of the allele at one of the sites tends to predict the presence of the allele at the other site on the same chromosome (Stevens, *Mol. Diag.* 4:309-17 (1999)). The marker loci can be located within 5 cM, 2 cM, or 1 cM (on a single meiosis based genetic map) of the gray leaf spot resistance trait QTL.

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Plant Compositions

Maize plants identified and/or selected by any of the methods described above are also of interest. This includes any plant from the species *Zea mays* that has within its genome a haplotype on chromosome 4 that comprises: a "T" at PHM521-8; a "G" at PHM12024-9; a "T" at PHM199-23; a "T" at PHM586-10; a "C" at PHM1963-15; a "G" at PHM18451-2; and a "C" at PHM289-20; and exhibits gray leaf spot resistance (the resistance can be newly conferred or enhanced) when compared to a maize plant that does not have the haplotype in its genome.

Seed Treatments

To protect and to enhance yield production and trait technologies, seed treatment options can provide additional crop plan flexibility and cost effective control against insects, weeds and diseases, thereby further enhancing the subject matter described herein. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *bacillus* spp. (including one or more of *cereus, firmus, megaterium, pumilis, sphaericus, subtilis* and/or *thuringiensis*), bradyrhizobium spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluquinconazole, flurazole, fluxofenim, harpin protein, imazalil, imidacloprid, ipconazole, isoflavenoids, lipochitooligosaccharide, mancozeb, manganese, maneb, mefenoxam, metalaxyl, metconazole, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, trichoderma, trifloxystrobin, triticonazole and/or zinc. PCNB seed coat refers to EPA registration number 00293500419, containing quintozen and terrazole. TCMTB refers to 2-(thiocyanomethylthio) benzothiazole.

Seeds that produce plants with specific traits (such as gray leaf spot resistance) may be tested to determine which seed treatment options and application rates may complement such plants in order to enhance yield. For example, a plant with good yield potential but head smut susceptibility may benefit from the use of a seed treatment that provides protection against head smut, a plant with good yield potential but cyst nematode susceptibility may benefit from the use of a seed treatment that provides protection against cyst nematode, and so on. Further, the good root establishment and early emergence that results from the proper use of a seed treatment may result in more efficient nitrogen use, a better ability to withstand drought and an overall increase in yield potential of a plant or plants containing a certain trait when combined with a seed treatment.

EXAMPLES

The following examples are offered to illustrate, but not to limit, the claimed subject matter. It is understood that the examples and embodiments described herein are for illustrative purposes only, and persons skilled in the art will recognize various reagents or parameters that can be altered without departing from the spirit of the disclosure or the scope of the appended claims.

Example 1

Mapping and Validation of a QTL for Gray Leaf Spot

A region of the maize genome on chromosome 4 at 100-115 cM on a single meiosis-based genetic map was found to be associated with gray leaf spot in a QTL mapping study. To investigate the QTL region further, a gray leaf susceptible proprietary inbred line (referred to herein as "Inbred B"), was crossed with a resistant proprietary inbred (referred to herein as "Inbred A") to generate a $BC_4F_2$ population of 1600 plants. The seed was bulked after selfing the last backcross and then planted. The plants were inoculated with *Cercospora zeae-maydis* infested maize seed as the carrier. Inoculations were done by dropping 5-10 infested seeds into leaf whorls at the V5-6 and again at V8 growth stage. Disease scoring was done by rating plants on a 1-9 scale with 1 as the worst and 9 as the best. Check plots with known disease response were used as a guide for the best time to score and for rating calibration. Scoring was done twice. Flowering data was also taken by noting the date on which 50% of each plant showed silks and converting this to a growing degree heat unit score (GDUSLK) based upon weather data at that location.

Of the 1633 plants in the field, 1607 were genotyped at 5 markers across a region of chromosome 4; these markers were PHM6764-7 (94.78 cM on single meiosis based genetic map), PHM16360-9 (104.12 cM), PHM521-8 (108.38 cM), PHM586-10 (111.72 cM), and PHM289-20 (113.94 cM). Differences were observed between plants with either one or two copies of the donor parent allele and plants with no copies of the donor parent allele (Table 1). Two copies of the donor parent allele showed a difference of 0.62 points and one copy showed a difference of 0.79 on the 1-9 scale (Table 2). Plants with no copies of the donor parent allele had an average score of 4.64 (Table 2). There were no differences in flowering time between the classes.

TABLE 1

Genotypes of parents at markers PHM6764-7, PHM16360-9, PHM521-8, PHM586-10, and PHM289-20

| Marker | Genetic Position (internal single meiosis map, cM) | Genetic Position (IBM2, cM) | Reference sequence ID | Donor Parent "Inbred A" | Recurrent Parent "Inbred B" | SNP Position in Reference Sequence |
|---|---|---|---|---|---|---|
| PHM6764-7 | 94.78 | 261.3 | SEQ ID NO: 1 | A | G | 150 |
| PHM16360-9 | 104.12 | 287.0 | SEQ ID NO: 2 | G | C | 231 |
| PHM521-8 | 108.38 | 299.3 | SEQ ID NO: 3 | T | C | 244 |
| PHM586-10 | 111.72 | 304.3 | SEQ ID NO: 4 | T | C | 114 |
| PHM289-20 | 113.94 | 331.3 | SEQ ID NO: 5 | C | T | 121 |

TABLE 2

Gray leaf spot scores of each genotypic class in the QTL area

| | Plants | GLS Score |
|---|---|---|
| Recurrent Parent | 187 | 4.64 (0) |
| Donor Parent | 165 | 5.26 (+0.62) |
| Heterozygotes | 482 | 5.44 (+0.79) |

Example 2

Further Refinement of QTL

The same methods were used to evaluate $BC_2$ individual plants from 3 additional recurrent parents (PH18F6 (see U.S. Pat. No. 8,766,059), PH18G5 see U.S. Pat. No. 8,304,633), and a third proprietary inbred referred to herein as "Inbred C") in order to determine the donor parent ("Inbred A") effect in different backgrounds. Additional markers were used in the 108-114 cM (299-331 cM for IBM2 map) region across all populations. Markers used and genotypes for each recurrent parent and the donor are shown in Table 3. Some of these markers are monomorphic for some donor/recurrent parent combinations. This testing again showed differences between those plants with one copy of the donor parent allele vs those with two copies of the recurrent parent allele (Table 4). Differences ranged from 1.5 points on the 1-9 scale to 2.5 points. The susceptible recurrent parents had scores ranging from 3.7 to 4.3.

TABLE 3

Markers and genotypes for donor and recurrent parents

| Marker | Genetic Position (internal single meiosis map, cM) | Genetic Position (IBM2, cM) | Reference Sequence ID Number | Inbred A | Inbred C | PH18F6 | PH18G5 | SNP Position in Reference Sequence |
|---|---|---|---|---|---|---|---|---|
| PHM521-8 | 108.38 | 299.9 | SEQ ID NO: 3 | T | C | C | C | 244 |
| PHM12024-9 | 109.01 | 299.9 | SEQ ID NO: 6 | G | C | C | C | 190 |
| PHM199-23 | 110.5 | 304.3 | SEQ ID NO: 7 | T | A | T | T | 243 |
| PHM586-10 | 111.72 | 304.3 | SEQ ID NO: 4 | T | C | T | T | 114 |
| PHM1963-15 | 111.72 | 304.3 | SEQ ID NO: 8 | C | C | T | T | 71 |
| PHM15534-13 | 111.88 | 304.3 | SEQ ID NO: 28 | C | T | T | T | 50 |
| PHM18451-2 | 113.64 | 330.4 | SEQ ID NO: 9 | G | A | A | A | 233 |
| PHM289-20 | 113.94 | 331.3 | SEQ ID NO: 5 | C | T | T | T | 121 |

TABLE 4

Gray leaf spot scores for each genotypic class in the QTL area

| | GLFSPT | Score Difference | GDUSLK | Count |
|---|---|---|---|---|
| Inbred C < [Inbred A] | | | | |
| RP allele across region | 4.1 | | 141.1 | 49 |
| Het across region | 6.6 | 2.5 | 139.8 | 17 |
| PH18F6 < [Inbred A] | | | | |
| RP allele across region | 3.7 | | 138.7 | 45 |
| Het across region | 5.9 | 2.2 | 139.1 | 39 |
| PH18G5 < [Inbred A] | | | | |
| RP allele across region | 4.3 | | 141.4 | 64 |
| Het across region | 5.8 | 1.5 | 141.9 | 22 |

RP = recurrent parent
Het = heterozygous

Further analysis of the region around PHM586-10 was performed because it is close to the QTL identified in patent application US2009172845. Inbred A and PHJEP (in patent application US2009172845) have different polymorphisms at PHM1963-15 at 111.72 cM (internal map, 304.3 cM on IBM2 map). In addition, further marker analysis near the peak marker (Table 5) shows that Inbred A and PHJEP are different in the region, indicating that Inbred A is a new source of resistance.

TABLE 5

Marker analysis near peak marker

| Marker | Reference Sequence Seq ID NO: | Genetic Position (internal single meiosis map, cM) | Genetic Position (IBM2, cM) | SNP Position in Reference Sequence | Inbred A | PHJEP |
|---|---|---|---|---|---|---|
| PZE-104068674 | SEQ ID NO: 10 | 111.45 | 304.3 | 51 | A\A | A\A |

TABLE 5-continued

Marker analysis near peak marker

| Marker | Reference Sequence Seq ID NO: | Genetic Position (internal single meiosis map, cM) | Genetic Position (IBM2, cM) | SNP Position in Reference Sequence | Inbred A | PHJEP |
|---|---|---|---|---|---|---|
| SYN25809 | SEQ ID NO: 11 | 111.52 | 304.3 | 61 | C\C | T\T |
| PZE-104069351 | SEQ ID NO: 12 | 111.55 | 304.3 | 51 | G\G | A\A |
| PZE-104069548 | SEQ ID NO: 13 | 111.57 | 304.3 | 51 | A\A | A\A |
| PZE-104069570 | SEQ ID NO: 14 | 111.59 | 304.3 | 51 | A\A | G\G |
| PZE-104069652 | SEQ ID NO: 15 | 111.62 | 304.3 | 51 | T\T | C\C |
| SYN21168 | SEQ ID NO: 16 | 111.68 | 304.3 | 61 | G\G | T\T |
| SYN4720 | SEQ ID NO: 17 | 111.72 | 304.3 | 61 | G\G | A\A |
| SYN4714 | SEQ ID NO: 18 | 111.74 | 304.3 | 61 | T\T | T\T |
| PZE-104070450 | SEQ ID NO: 19 | 112.5 | 323.2 | 51 | C\C | G\G |

TABLE 6

Marker haplotypes in the current mapping interval with GLS scores for each haplotype and recombinants.

| Plant ID | PHMGLS_01 | PHMGLS_07 | PHMGLS_14 | PHMGLS_19 | PHMGLS_21 |
|---|---|---|---|---|---|
| Donor Parent Inbred A | T | C | G | C | C |
| Inbred C | A | T | A | T | T |
| 419 | T | C | G | C | C |
| 373 | T | C | G | C | C |
| 312 | T | C | G | C | C |
| 316 | T | C | G | C | C |
| 256 | T/A | C/T | G/A | C/T | C |
| 253 | T | C | G | C | C |
| 207 | T | C | G | C | C |
| 211 | T | C | G | C | C |
| 159 | T | C | G | C | C |
| 103 | T | C | G | C | C |
| 86 | T | C | G | C | C |
| Class mean | — | — | — | — | — |
| 223 | T | C | G | C | C |
| 121 | A | T | A | T | C |
| 120 | A | T | A | T | C |
| | — | — | — | — | — |
| 239 | A | T | A | T | T |
| 270 | A | T | A | T | T |
| 406 | A | T | A | T | T |
| 282 | A | T | A | T | T |
| 47 | A | T | A | T | T |
| 46 | A | T | A | T | T |
| 31 | A | T | A | T | T |
| 9 | A | T | A | T | T |
| 391 | A | T | A | T | T |
| Class mean | — | — | — | — | — |

| Plant ID | PHMGLS_45 | PHMC001001YAR | PHM5013-12 | 4 Location Blup |
|---|---|---|---|---|
| Donor Parent Inbred A | C | A | C | — |
| Inbred C | T | G | T | — |
| 419 | C | A | C | 5.73 |
| 373 | C | A | C | 5.22 |
| 312 | C | A | C | 5.62 |
| 316 | C | A | C | 5.5 |
| 256 | C | A | C | 5.68 |
| 253 | C | A | C | 5.09 |
| 207 | C | A | C | 5.44 |
| 211 | C | A | C | 5.08 |
| 159 | C | A | C | 5.43 |
| 103 | C | A | C | 5.87 |
| 86 | C | A | C | 5.08 |

TABLE 6-continued

Marker haplotypes in the current mapping interval with GLS scores for each haplotype and recombinants.

| | | | | |
|---|---|---|---|---|
| Class mean | — | — | — | 5.43 |
| 223 | C | G | T | 5.65 |
| 121 | C | A | C | 5.84 |
| 120 | C | A | C | 5.79 |
| 239 | T | G | T | 4.58 |
| 270 | T | G | T | 4.37 |
| 406 | T | G | T | 4.76 |
| 282 | T | G | T | 4.15 |
| 47 | T | G | T | 4.48 |
| 46 | T | G | T | 4.4 |
| 31 | T | G | T | 4.2 |
| 9 | T | G | T | 4.61 |
| 391 | T | G | T | 3.64 |
| Class mean | — | — | — | 4.35 |

What is claimed is:

1. A method of identifying and/or selecting a maize plant that displays increased resistance to gray leaf spot, said method comprising:
   a) detecting in a maize plant an allele of a marker locus, wherein said marker locus is located within a chromosomal interval on chromosome 4 comprising and flanked by PHM6764-7 and PHM289-20 and said allele comprises a haplotype comprising a "T" at PHM521-8 at position 244 of SEQ ID NO: 3; a "G" at PHM12024-9 at position 190 of SEQ ID NO: 6; a "T" at PHM199-23 at position 243 of SEQ ID NO:7; a "T" at PHMGLS_01 at position 51 of SEQ ID NQ:20; a "C" at PHMGLS_07 at position 51 of SEQ ID NO:21; a "G" at PHMGLS-14 at position 51 of SEQ ID NO:22; a "C" at PHMGLS_19 at position 51 of SEQ ID NO:23; a "C" at PHMGLS_21 at position 51 of SEQ ID NO:24; a "C" at PHMGLS_45 at position 51 of SEQ ID NO:25; a "A" at PHMC001YAR at position 51 of SEQ ID NO:26; a "C" at PHM5013-12 at position 50 of SEQ ID NO:27; a "T" at PHM586-10 at position 114 of SEQ ID NO:4; a "C" at PHM1963-15 at position 71 of SEQ ID NO:8; a "C" at PHM15534-13 at position 50 of SEQ ID NO:28; a "G" at PHM18451-2 at position 233 of SEQ ID NO:9; and a "C" at PHM289-20 at position 121 of SEQ ID NO:5;
   b) selecting a maize plant that has the allele of the marker locus that comprises the haplotype comprising: a "T" at PHM521-8 at position 244 of SEQ ID NO:3: a "G" at PHM12024-9 at position 190 of SEQ ID NO:6; a "T" at PHM199-23 at position 243 of SEQ ID NO:7; a "T" at PHMGLS_01 at position 51 of SEQ ID NO:20; a "C" at PHMGLS_07 at position 51 of SEQ ID NO:21; a "G" at PHMGLS 14 at position 51 of SEQ ID NO:22; a "C" at PHMGLS_19 at position 51 of SEQ ID NO:23; a "C" at PHMGLS_21 at position 51 of SEQ ID NO:24; a "C" at PHMGLS_45 at position 51 of SEQ ID NO:25; a "A" at PHMC001YAR at position 51 of SEQ ID NO:26; a "C" at PHM5013-12 at position 50 of SEQ ID NO:27; a "T" at PHM586-10 at position 114 of SEQ ID NO:4; a "C" at PHM1963-15 at position 71 of SEQ ID NO:8; a "C" at PHM15534-13 at position 50 of SEQ ID NO:28; a "G" at PHM18451-2 at position 233 of SEQ ID NO:9; and a "C" at PHM289-20 at position 121 of SEQ ID NO:5;
   c) crossing the maize plant of (b) with a second maize plant; and
   d) obtaining a progeny plant that has the allele that comprises the haplotype comprising a "T" at PHM521-8 at position 244 of SEQ ID NO: 3; a "G" at PHM12024-9 at position 190 of SEQ ID NO: 6; a "T" at PHM199-23 at position 243 of SEQ ID NO: 7; a "T" at PHMGLS_01 at position 51 of SEQ ID NO: 20; a "C" at PHMGLS_07 at position 51 of SEQ ID NO: 21; a "G" at PHMGLS_14 at position 51 of SEQ ID NO: 22; a "C" at PHMGLS_19 at position 51 of SEQ ID NO: 23; a "C" at PHMGLS_21 at position 51 of SEQ ID NO: 24; a "C" at PHMGLS_45 at position 51 of SEQ ID NO: 25; a "A" at PHMC001YAR at position 51 of SEQ ID NO: 26; a "C" at PHM5013-12 at position 50 of SEQ ID NO: 27; a "T" at PHM586-10 at position 114 of SEQ ID NO: 4; a "C" at PHM1963-15 at position 71 of SEQ ID NO: 8; a "C" at PHM15534-13 at position 50 of SEQ ID NO: 28; a "G" at PHM18451-2 at position 233 of SEQ ID NO: 9; and a "C" at PHM289-20 at position 121 of SEQ ID NO: 5; wherein the progeny plant has increased resistance to gray leaf spot.

2. The method of claim 1, wherein said marker locus is located within a chromosomal interval on chromosome 4 comprising and flanked by PHM521-8 and PHM18451-2.

3. A method of identifying and/or selecting a maize plant that displays increased resistance to gray leaf spot, said method comprising:
  a) detecting in a maize plant a "T" at PHM521-8 at position 244 of SEQ ID NO: 3; a "G" at PHM12024-9 at position 190 of SEQ ID NO: 6; a "T" at PHM199-23 at position 243 of SEQ ID NO: 7; a "T" at PHMGLS_01 at position 51 of SEQ ID NO: 20; a "C" at PHMGLS 07 at position 51 of SEQ ID NO: 21; a "G" at PHMGLS_14 at position 51 of SEQ ID NO: 22; a "C" at PHMGLS_19 at position 51 of SEQ ID NO: 23; a "C" at PHMGLS_21 at position 51 of SEQ ID NO: 24; a "C" at PHMGLS_45 at position 51 of SEQ ID NO: 25; a "A" at PHMC001YAR at position 51 of SEQ ID NO: 26; a "C" at PHM5013-12 at position 50 of SEQ ID NO: 27; a "T" at PHM586-10 at position 114 of SEQ ID NO: 4; a "C" at PHM1963-15 at position 71 of SEQ ID NO: 8; a "C" at PHM15534-13 at position 50 of SEQ ID NO: 28; a "G" at PHM18451-2 at position 233 of SEQ ID NO: 9; and a "C" at PHM289-20 at position 121 of SEQ ID NO: 5;
  b) selecting said maize plant that has a "T" at PHM521-8 at position 244 of SEQ ID NO: 3; a "G" at PHM12024-9 at position 190 of SEQ ID NO: 6; a "T" at PHM199-23 at position 243 of SEQ ID NO: 7; a "T" at PHMGLS_01 at position 51 of SEQ ID NO: 20; a "C" at PHMGLS_07 at position 51 of SEQ ID NO: 21; a "G" at PHMGLS_14 at position 51 of SEQ ID NO: 22; a "C" at PHMGLS_19 at position 51 of SEQ ID NO: 23; a "C" at PHMGLS_21 at position 51 of SEQ ID NO: 24; a "C" at PHMGLS_45 at position 51 of SEQ ID NO: 25; a "A" at PHMC001YAR at position 51 of SEQ ID NO: 26; a "C" at PHM5013-12 at position 50 of SEQ ID NO: 27; a "T" at PHM586-10 at position 114 of SEQ ID NO: 4; a "C" at PHM1963-15 at position 71 of SEQ ID NO: 8; a "C" at PHM15534-13 at position 50 of SEQ ID NO: 28; a "G" at PHM18451-2 at position 233 of SEQ ID NO: 9; and a "C" at PHM289-20 at position 121 of SEQ ID NO: 5;
  c) crossing the maize plant of (b) with a second maize plant; and
  d) obtaining a progeny plant that has the allele that comprises the haplotype comprising a "T" at PHM521-8 at position 244 of SEQ ID NO: 3; a "G" at PHM12024-9 at position 190 of SEQ ID NO: 6; a "T" at PHM199-23 at position 243 of SEQ ID NO: 7; a "T" at PHMGLS_01 at position 51 of SEQ ID NO: 20; a "C" at PHMGLS_07 at position 51 of SEQ ID NO: 21; a "G" at PHMGLS_14 at position 51 of SEQ ID NO: 22; a "C" at PHMGLS_19 at position 51 of SEQ ID NO: 23; a "C" at PHMGLS_21 at position 51 of SEQ ID NO: 24; a "C" at PHMGLS_45 at position 51 of SEQ ID NO: 25; a "A" at PHMC001YAR at position 51 of SEQ ID NO: 26; a "C" at PHM5013-12 at position 50 of SEQ ID NO: 27; a "T" at PHM586-10 at position 114 of SEQ ID NO: 4; a "C" at PHM1963-15 at position 71 of SEQ ID NO: 8; a "C" at PHM15534-13 at position 50 of SEQ ID NO: 28; a "G" at PHM18451-2 at position 233 of SEQ ID NO: 9; and a "C" at PHM289-20 at position 121 of SEQ ID NO: 5; wherein said maize plant has increased resistance to gray leaf spot.

\* \* \* \* \*

SEQUENCE LISTING

<160> NUMBER OF SEQ ID NOS: 28

<210> SEQ ID NO 1
<211> LENGTH: 374
<212> TYPE: DNA
<213> ORGANISM: Artificial
<220> FEATURE:
<223> OTHER INFORMATION: PHM6764-7 Reference Sequence
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (210)..(211)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (238)..(239)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t

<400> SEQUENCE: 1
cacagccagc agagttccag aggtgtatgg tgccactttt tcgtcagatt tcccgatgtt     60
taagcagttc tcactttcag gtaagaagag atagcagact gcnagttaca caatataaat    120
atagtatatt tacttgttaa tagttcatcr aagttctcat cttcaaattt atcattgatt    180
tctgccttat tgcttgggac atgatgactn natcatttat tngtttataa gtgcaagnna    240
actaagctgt agcaagcgat aggtgtaaag cgcatactac tattttgttg atgttgatac    300
acaaatagta atattnacct ttctagctgc cacttacaca tgatgacatg ttagtagtgt    360
gggaactttg tcca                                                      374

<210> SEQ ID NO 2
<211> LENGTH: 362
<212> TYPE: DNA
<213> ORGANISM: Artificial
<220> FEATURE:
<223> OTHER INFORMATION: PHM16360-9 Reference Sequence
<220> FEATURE:
<221> NAME/KEY: misc_feature

```
<222> LOCATION: (15)..(15)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (172)..(173)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t

<400> SEQUENCE: 2
aagatccgcg acacnggacc ggancggcag atggaggagg cgctcaggat cgcctacctg    60
tgcaccgcgg agctgccgtc caagaggccc gccatgcagc agatcgtngg ccttctcaag   120
gacatcgagc cgaaggtgga agaggagggg gactgaagat ctggaggagt gnnatcggnt   180
gcacctngca gcgtgtcgga tggtggtgag atttgtgtag tgacagcgtc sgcaggcagg   240
caggctgtga ctgtgagtga gctcgtggtt gttttaccat cgtcgagctc actatgccat   300
gccttgctct gcatatatct ttttcatcct tctttcttcc cttttncccg cttctntctc   360
gc                                                                  362

<210> SEQ ID NO 3
<211> LENGTH: 395
<212> TYPE: DNA
<213> ORGANISM: Artificial
<220> FEATURE:
<223> OTHER INFORMATION: PHM521-8 Reference Sequence

<400> SEQUENCE: 3
agtgagaaag gaaatcaacc catcttgcag cagcatagtt gcagggaagg gcaactgcat    60
cgtctactct tctgatggga agcggtttga gatccccctt tcttacctcc acacggcagt   120
gtttgtagag ctcctgaagc tgtcgcagga agagtttggg ttcacaagtg atgggaggat   180
cacactgcct tgcgataaag cagtgatgga gtatgtgatg tgtttgctaa ggagagaagc   240
ctcygaggat gttgagaagg cgctcctcag ttccatagtg atgtcttgcc accacacaaa   300
caggatggtg caaccaccaa gtggagtgaa ccaccacttc gctgtgtgca gctcctgaag   360
atgaagatat ccatggcttg gagcttgttt cagca                              395

<210> SEQ ID NO 4
<211> LENGTH: 374
<212> TYPE: DNA
<213> ORGANISM: Artificial
<220> FEATURE:
<223> OTHER INFORMATION: PHM586-10 Reference Sequence
```

<400> SEQUENCE: 4

```
gcagctcggc gtcaggtcyt ggcccaagtg agcaccgctg ccgccgatca ctgyccgcta    60
gtttacttct tggtytctcg tccccagctc ctgatcgccg tggcgtatgt aacygctgcc   120
gtgcgtgtgc aggtggggtt gcccgccggg gaagttccgg tgaagttcg acgcgcggca    180
gacgtgctac ctgctcaagg gcaaggtgcg ggcgcacatc aaggggtcgt cggagtgcgt   240
ggagttcggc gccggcgacc tcgtcgtctt ccccaagggk ctcagctgca cctgggacgt   300
cgccgccgcc gtcgacaagt actacaagtt cgactcgtcc tgacggctga cgcacatcgc   360
tcccgcccgg ctcc                                                     374
```

<210> SEQ ID NO 5
<211> LENGTH: 183
<212> TYPE: DNA
<213> ORGANISM: Artificial
<220> FEATURE:
<223> OTHER INFORMATION: PHM289-20 Reference Sequence

<400> SEQUENCE: 5

```
cgtcatcgag aagaaagcca aggggacaga agaagaagaa cgtgtgtggg cgtgggagat    60
ggtggagcca ctcatgacca aagcgctcac caccatgccc tacctcaacg aatacaaggt   120
ycctgaacct gaacctgaac ctgaacccat cccttgaact tctgcactgc agagtctccg   180
gat                                                                 183
```

<210> SEQ ID NO 6
<211> LENGTH: 373
<212> TYPE: DNA
<213> ORGANISM: Artificial
<220> FEATURE:
<223> OTHER INFORMATION: PHM12024-9 Reference Sequence

<400> SEQUENCE: 6

```
cccctcttgg atgtcggtca tgggaggcaa tgcacgctcc ttgggacttg taagagttat    60
ctgttttgtt gcttcgcggg cccaaaggac gcttccctgc accatctgcc tttgtttgga   120
acggcttgga ccgccgtggt ccttttacct gcagcaagga aaggaatggc tgggagggaa   180
tggatactgs tatcgttccg tgtgtggcac cccgtgatct gtttgccgtg ctttgtagga   240
ggcatggcgt attgccgggt actttggttt tggagactgc tactgactgc tgmcgtcgtc   300
gggccgctcc tctcacctct ggtaaatagg actttgtaca caattatttt gttagtagca   360
gtatatgtac atc                                                      373
```

<210> SEQ ID NO 7
<211> LENGTH: 350
<212> TYPE: DNA
<213> ORGANISM: Artificial
<220> FEATURE:
<223> OTHER INFORMATION: PHM199-23 Reference Sequence
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature

```
<222> LOCATION: (295)..(295)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t

<400> SEQUENCE: 7
ttatcaggtg gcactcctct gcacgcaggg ctcccgttgg agcgtccaaa gatgtcggag      60
gtggtgagga tgctggaagg tgacggcctg gcagagcgtt gggacgaatg cagaaagta     120 gaggtggtga ggcaggaggc ngantcggca ccgctccgca atgactggat cgtcgattcc    180
acgtacaacc ttcgtgcngt ggagctgtcc ggtccaaggt agtagccact ccatgactcc    240
gawgaaagaa ttcaacactg aattgcctag attcagtcta attgctgctt gtgtntatga    300
aaggtagctt ttggaattgt tagcgncagt caatatgaag ggatgttttt              350

<210> SEQ ID NO 8
<211> LENGTH: 361
<212> TYPE: DNA
<213> ORGANISM: Artificial
<220> FEATURE:
<223> OTHER INFORMATION: PHM1963-15 Reference Sequence
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (332)..(335)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t

<400> SEQUENCE: 8
ggtgctttnc gcgggcagtc ncaaataaac cagattttgt gcagctgaac atcaatggaa     60
attttatctc ygatgaaggg gttgatgagg tgaaggaaat tctgaaggct ggtaagaaat    120
ctctngatgt gctgggccca ctagacgaga atgaacctga tggagagcct gatgatgagg    180
atgcngagga cgatgaggac nagctggatt tgaanctgca gagtgtgaag gttgagcagg    240
```

```
atgaggatga ttgacgatcc ttaggttaaa tatctttagc tactcagtaa tcatttggat    300
ntccatgagc tacgcaaact tttaattaaa annnntntac tgagnctttt gcattgtcct    360
g                                                                    361
```

<210> SEQ ID NO 9
<211> LENGTH: 363
<212> TYPE: DNA
<213> ORGANISM: Artificial
<220> FEATURE:
<223> OTHER INFORMATION: PHM18451-2 Reference Sequence

<400> SEQUENCE: 9

```
ataaaatacg tacttcattt aagtaagcgc caagagattg aaggattaat ggtggccata     60
actttatgca gaatttcatt gccatgatct taccagtcac aagtgttacc ccatgttgtc    120
aacttggcat aatcgttgac ctggaagttt aacggttgaa ccagggaccg gcatgcagct    180
ccatttcttt tttggtgtgt gtccatggat caaagagcag cgccgtggtt ggrcattttt    240
acccttcctt tggtttaggt gaaagttgga cctctgtagc tcggagtctt agcaggtagc    300
cagttttwat ttctgataag tttttaggca agttgtaagt tgtagcacaa aatcgatcac    360
ttg                                                                  363
```

<210> SEQ ID NO 10
<211> LENGTH: 101
<212> TYPE: DNA
<213> ORGANISM: Artificial
<220> FEATURE:
<223> OTHER INFORMATION: PZE-104068674 Reference Sequence

<400> SEQUENCE: 10

```
caagcaggag cgatgggcac ctcaccggag aacatgaatt atgtgacccg rtcacctaaa     60
tccaaatcta acagacgcta ctcgaagtaa ggaagacaac a                        101
```

<210> SEQ ID NO 11
<211> LENGTH: 121
<212> TYPE: DNA
<213> ORGANISM: Artificial
<220> FEATURE:
<223> OTHER INFORMATION: SYN25809 Reference Sequence

<400> SEQUENCE: 11

```
gaatcacaaa atctttgcac cttatcactc agctcgggtt gaaccagcgg ccgccagtcg     60
ygctgttcat gtggtgcccg ttcccgtgca tccctgcacc gtttggtgcc attggggatg    120
c                                                                    121
```

<210> SEQ ID NO 12
<211> LENGTH: 101
<212> TYPE: DNA
<213> ORGANISM: Artificial
<220> FEATURE:
<223> OTHER INFORMATION: PZE-104069351 Reference Sequence

<400> SEQUENCE: 12

```
gtgtcttact agtaggctct atatatgcgt ggtgtgggct gccgtgccgt rccatcactg     60
ctctcctgcc ctcctcttta taaacagcgc gcaacgaggg a                        101
```

<210> SEQ ID NO 13
<211> LENGTH: 101
<212> TYPE: DNA
<213> ORGANISM: Artificial

```
<220> FEATURE:
<223> OTHER INFORMATION: PZE-104069548 Reference Sequence

<400> SEQUENCE: 13
attacgatgg ggaaatccag gggcgaccgc ttcgtaatct tctcctcatc rggggccgcg      60
cagaccacga gggcgttcca cctgcaccgc ttacttccgg g                         101

<210> SEQ ID NO 14
<211> LENGTH: 101
<212> TYPE: DNA
<213> ORGANISM: Artificial
<220> FEATURE:
<223> OTHER INFORMATION: PZE-104069570 Reference Sequence

<400> SEQUENCE: 14
cagctgcgag acggtaaccg cctcagggtc ctcgctgcga aactgttttt raaatccta      60 gggcctcatc tgcacgttta gcatccaact ttcagtttcc a                         101

<210> SEQ ID NO 15
<211> LENGTH: 101
<212> TYPE: DNA
<213> ORGANISM: Artificial
<220> FEATURE:
<223> OTHER INFORMATION: PZE-104069652 Reference Sequence

<400> SEQUENCE: 15
aggcctttat tgagatcatc tttctctcac cttcaacccg agcccttccc yagtcatgtt      60
ggctgcctag agtgtcattc tggctgactc gagcgagggt c                         101

<210> SEQ ID NO 16
<211> LENGTH: 121
<212> TYPE: DNA
<213> ORGANISM: Artificial
<220> FEATURE:
<223> OTHER INFORMATION: SYN21168 Reference Sequence
<220> FEATURE:
<221> NAME/KEY: misc_feature
<222> LOCATION: (83)..(83)
<223> OTHER INFORMATION: n is a, c, g, or t

<400> SEQUENCE: 16
tcttatctcc tcctgccggc gatccgcagt agaaccccac ataggtcgtt tctccgcaga      60
katcatgacc aatccaggtg gcngtgacgt tcttggggtc gctaatgatg gtgttcttga     120
a                                                                    121

<210> SEQ ID NO 17
<211> LENGTH: 121
<212> TYPE: DNA
<213> ORGANISM: Artificial
<220> FEATURE:
<223> OTHER INFORMATION: SYN4720 Reference Sequence

<400> SEQUENCE: 17
tttctctgaa gggatgatca gtggcgttat attaatatta ctgatgatgt cggggatgtt      60
ragcccgttg gagaagcggc ccgtggcttg gtgcgtgggg aagtcgatgc cgtagggggg     120
c                                                                    121

<210> SEQ ID NO 18
<211> LENGTH: 121
<212> TYPE: DNA
<213> ORGANISM: Artificial
<220> FEATURE:
```

<223> OTHER INFORMATION: SYN4714 Reference Sequence

<400> SEQUENCE: 18
gcccagcatc tcgctcttct caaacgggct atccattttt ccaaacagca tgcgactcct    60
ytctgaactt ctacccagga tcccgcggaa cttctcagca gtattggttg gagagaccct   120
a                                                                  121

<210> SEQ ID NO 19
<211> LENGTH: 101
<212> TYPE: DNA
<213> ORGANISM: Artificial
<220> FEATURE:
<223> OTHER INFORMATION: PZE-104070450 Reference Sequence
<220> FEATURE:
<221> NAME/KEY: misc_feature
<222> LOCATION: (51)..(51)
<223> OTHER INFORMATION: n is a, c, g, or t

<400> SEQUENCE: 19
acaatttgtt taactcagta accgtatgtc cgtatgtatg ctgtttagta nctacatgtg    60
atgtgcttca gttcgttgtt ttctgcttct gctcttcctt g                       101

<210> SEQ ID NO 20
<211> LENGTH: 102
<212> TYPE: DNA
<213> ORGANISM: Artificial
<220> FEATURE:
<223> OTHER INFORMATION: PHMGLS_01 Reference Sequence
<220> FEATURE:
<221> NAME/KEY: misc_feature
<222> LOCATION: (51)..(51)
<223> OTHER INFORMATION: n is a, c, g, or t

<400> SEQUENCE: 20
actgatagga gccgatgccg aaaacccatt cttctagcat cctacttgat ngctacgtat    60
atatgccaga actggatgga tggatggatg gatggccatt gt                     102

<210> SEQ ID NO 21
<211> LENGTH: 102
<212> TYPE: DNA
<213> ORGANISM: Artificial
<220> FEATURE:
<223> OTHER INFORMATION: PHMGLS_07 Reference Sequence
<220> FEATURE:
<221> NAME/KEY: misc_feature
<222> LOCATION: (51)..(51)
<223> OTHER INFORMATION: n is a, c, g, or t

<400> SEQUENCE: 21
ttaaaaactg aatttctact acatttggtt tatgtacctg ccctaagatg nccttctcctg   60 tctgagcctc cactagcaat ccagccgtga gtcctatcac tg                     102

<210> SEQ ID NO 22
<211> LENGTH: 102
<212> TYPE: DNA
<213> ORGANISM: Artificial
<220> FEATURE:
<223> OTHER INFORMATION: PHMGLS_14 Reference Sequence
<220> FEATURE:
<221> NAME/KEY: misc_feature
<222> LOCATION: (51)..(51)
<223> OTHER INFORMATION: n is a, c, g, or t

<400> SEQUENCE: 22
agcaggagga gccagaagaa caagaggctg agagaggagg aatcgacgcc nagaagcaga    60

```
gaccggtgga gcacgccatt cttgctgccc ccgcctccct gg                          102
```

<210> SEQ ID NO 23
<211> LENGTH: 102
<212> TYPE: DNA
<213> ORGANISM: Artificial
<220> FEATURE:
<223> OTHER INFORMATION: PHMGLS_19 Reference Sequence
<220> FEATURE:
<221> NAME/KEY: misc_feature
<222> LOCATION: (51)..(51)
<223> OTHER INFORMATION: n is a, c, g, or t

<400> SEQUENCE: 23

```
gaaacaactc ccaataccac tgattggaca cctattgtca cgcatgcttg nttgttggat      60
aaaaggcatc aagaacaaac aacagttgtg ctaccgctga gc                         102
```

<210> SEQ ID NO 24
<211> LENGTH: 102
<212> TYPE: DNA
<213> ORGANISM: Artificial
<220> FEATURE:
<223> OTHER INFORMATION: PHMGLS_21 Reference Sequence
<220> FEATURE:
<221> NAME/KEY: misc_feature
<222> LOCATION: (51)..(51)
<223> OTHER INFORMATION: n is a, c, g, or t

<400> SEQUENCE: 24

```
tacagtcatg tttgaacgtt atttttctag gctggacaga tcgtccacac nagatataat      60
gactctactg attatatcag atcgtcccaa gggaataatc at                         102
```

<210> SEQ ID NO 25
<211> LENGTH: 102
<212> TYPE: DNA
<213> ORGANISM: Artificial
<220> FEATURE:
<223> OTHER INFORMATION: PHMGLS_45 Reference Sequence
<220> FEATURE:
<221> NAME/KEY: misc_feature
<222> LOCATION: (51)..(51)
<223> OTHER INFORMATION: n is a, c, g, or t

<400> SEQUENCE: 25

```
tgcctaatca gcgtcgagca gctcaacctg gccggaaacc gcctctacgg ncaggtaccc      60
gacgcgctct gcaagcttgc tgggcccgct ggccgcctcg cc                         102
```

<210> SEQ ID NO 26
<211> LENGTH: 101
<212> TYPE: DNA
<213> ORGANISM: Artificial
<220> FEATURE:
<223> OTHER INFORMATION: PHMC001YAR Reference Sequence
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 26

```
aagantagcc tgctaaccca yttcttgctt tctcactgga attgtaatac ntgcagaagt      60
tcgattctat gagtcgacat ggtataaaaa gtggtagatt g                          101
```

```
<210> SEQ ID NO 27
<211> LENGTH: 99
<212> TYPE: DNA
<213> ORGANISM: Artificial
<220> FEATURE:
<223> OTHER INFORMATION: PHM5013-12 Reference Sequence
<220> FEATURE:
<221> NAME/KEY: misc_feature
<222> LOCATION: (50)..(50)
<223> OTHER INFORMATION: n is a, c, g, or t

<400> SEQUENCE: 27 ggccctccc cttttccggg ttcttcaaca gcttcgacgg cgccgatttn gacgacgacg      60
acctcgcctg agggaactsc crcccggttc ggtaacgga                            99

<210> SEQ ID NO 28
<211> LENGTH: 99
<212> TYPE: DNA
<213> ORGANISM: Artificial
<220> FEATURE:
<223> OTHER INFORMATION: PHM15534-13 Reference Sequence
<220> FEATURE:
<221> NAME/KEY: misc_feature
<222> LOCATION: (50)..(50)
<223> OTHER INFORMATION: n is a, c, g, or t

<400> SEQUENCE: 28
aaagttgcat gaagtatatt tatgcatgtt tgtgttcaaa actaacatcn taataattgt     60
gctccycttt ccatatgcag ttatgatcac tcgattcag                            99
```